United States Patent
Sosnowski et al.

(10) Patent No.: US 9,283,102 B2
(45) Date of Patent: Mar. 15, 2016

(54) GASTRIC SPACE FILLER DEVICE, DELIVERY SYSTEM, AND RELATED METHODS

(75) Inventors: Stephen Alexander Sosnowski, Vista, CA (US); Tyler John Holschlag, Carlsbad, CA (US); Daniel Eugene Kincade, Chula Vista, CA (US)

(73) Assignee: ReShape Medical, Inc., San Clemente, CA (US)

( * ) Notice: Subject to any disclaimer, the term of this patent is extended or adjusted under 35 U.S.C. 154(b) by 0 days.

(21) Appl. No.: 13/074,956

(22) Filed: Mar. 29, 2011

(65) Prior Publication Data

US 2011/0178544 A1   Jul. 21, 2011

Related U.S. Application Data

(63) Continuation of application No. 11/768,152, filed on Jun. 25, 2007, now Pat. No. 8,142,469.

(51) Int. Cl.
| | | |
|---|---|---|
| A61M 29/00 | (2006.01) | |
| A61F 5/00 | (2006.01) | |
| A61M 25/09 | (2006.01) | |
| A61M 25/01 | (2006.01) | |

(52) U.S. Cl.
CPC .............. *A61F 5/0089* (2013.01); *A61F 5/0033* (2013.01); *A61F 5/0036* (2013.01); *A61M 25/09* (2013.01); *A61M 2025/0177* (2013.01)

(58) Field of Classification Search
CPC .... A61F 5/0089; A61F 5/0036; A61F 5/0033
USPC .............. 606/191, 192, 195; 600/37
See application file for complete search history.

(56) References Cited

U.S. PATENT DOCUMENTS

| | | |
|---|---|---|
| 2,493,326 A | 1/1950 | Trinder |
| 4,133,315 A | 1/1979 | Berman et al. |
| 4,198,983 A | 4/1980 | Becker et al. |
| 4,246,893 A | 1/1981 | Berson |
| 4,356,824 A | 11/1982 | Vazquez |

(Continued)

FOREIGN PATENT DOCUMENTS

| | | |
|---|---|---|
| DE | 8708978 U1 | 11/1987 |
| EP | 0103481 | 3/1984 |

(Continued)

OTHER PUBLICATIONS

International Search Report; International Application No. PCT/US2011/024082, Applicant: ReShape Medical, Inc., Mailing Date Apr. 6, 2011, 10 pages.

(Continued)

*Primary Examiner* — Katherine Rodjom
(74) *Attorney, Agent, or Firm* — Perkins Coie LLP (57) ABSTRACT

According to features of the present disclosure, a gastric space filler device and methods effective for reducing stomach volume are disclosed. A gastric space filler comprising at least one inflatable space filler and a sleeve to prevent leakage out of the gastric space filler device is disclosed. The gastric space filler device may be inflated with an insufflation fluid and with mineral oil, which further has the effect of reducing leakage. Delivery systems and methods for inserting a gastric space filler device into a patient are also disclosed. Sheaths and methods for covering a gastric space filler device during delivery into a patient are also disclosed.

16 Claims, 7 Drawing Sheets

(56) References Cited

U.S. PATENT DOCUMENTS

| | | |
|---|---|---|
| 4,368,739 A | 1/1983 | Nelson, Jr. |
| 4,416,267 A | 11/1983 | Garren et al. |
| 4,465,072 A | 8/1984 | Taheri |
| 4,465,818 A | 8/1984 | Shirahata et al. |
| 4,485,805 A | 12/1984 | Foster, Jr. |
| 4,543,089 A | 9/1985 | Moss |
| 4,598,699 A | 7/1986 | Garren et al. |
| 4,694,827 A | 9/1987 | Weiner et al. |
| 4,723,547 A | 2/1988 | Kullas et al. |
| 4,899,747 A | 2/1990 | Garren et al. |
| 4,940,458 A | 7/1990 | Cohn |
| 5,073,347 A | 12/1991 | Garren et al. |
| 5,084,061 A | 1/1992 | Gau et al. |
| 5,123,840 A | 6/1992 | Nates |
| 5,234,454 A | 8/1993 | Bangs |
| 5,259,399 A | 11/1993 | Brown |
| 5,263,934 A | 11/1993 | Haak |
| 5,273,536 A | 12/1993 | Savas |
| 5,318,530 A | 6/1994 | Nelson, Jr. |
| 5,334,187 A | 8/1994 | Fischell et al. |
| 5,431,173 A | 7/1995 | Chin et al. |
| 5,496,271 A | 3/1996 | Burton et al. |
| 5,516,812 A | 5/1996 | Chu et al. |
| 5,575,772 A | 11/1996 | Lennox |
| 5,639,810 A | 6/1997 | Smith, III et al. |
| 5,643,209 A | 7/1997 | Fugoso et al. |
| 5,730,722 A | 3/1998 | Wilk |
| 5,779,728 A | 7/1998 | Lunsford et al. |
| 5,857,991 A | 1/1999 | Grothoff et al. |
| 5,876,376 A | 3/1999 | Schwab et al. |
| 5,904,701 A | 5/1999 | Daneshvar |
| 5,938,669 A | 8/1999 | Klaiber et al. |
| 5,976,073 A | 11/1999 | Ouchi |
| 5,993,473 A | 11/1999 | Chan et al. |
| 5,997,503 A | 12/1999 | Willis et al. |
| 6,050,274 A | 4/2000 | Gelardi et al. |
| 6,149,621 A | 11/2000 | Makihara |
| 6,179,878 B1 | 1/2001 | Duerig et al. |
| 6,254,355 B1 | 7/2001 | Gharib |
| 6,276,567 B1 | 8/2001 | Diaz et al. |
| 6,280,411 B1 | 8/2001 | Lennox |
| 6,423,058 B1 | 7/2002 | Edwards et al. |
| 6,427,089 B1 | 7/2002 | Knowlton |
| 6,454,785 B2 | 9/2002 | De Hoyos Garza |
| 6,524,234 B2 | 2/2003 | Ouchi |
| 6,535,764 B2 | 3/2003 | Imran et al. |
| 6,540,789 B1 | 4/2003 | Stein et al. |
| 6,547,788 B1 | 4/2003 | Maguire et al. |
| 6,579,301 B1 | 6/2003 | Bales et al. |
| 6,592,552 B1 | 7/2003 | Schmidt |
| 6,613,018 B2 | 9/2003 | Bagga et al. |
| 6,613,037 B2 | 9/2003 | Khosravi et al. |
| 6,689,051 B2 | 2/2004 | Nakada |
| 6,706,010 B1 | 3/2004 | Miki et al. |
| 6,746,460 B2 | 6/2004 | Gannoe et al. |
| 6,826,428 B1 | 11/2004 | Chen et al. |
| 6,850,128 B2 | 2/2005 | Park |
| 6,866,657 B2 | 3/2005 | Shchervinsky |
| 6,869,431 B2 | 3/2005 | Maguire et al. |
| 6,890,300 B2 | 5/2005 | Lloyd et al. |
| 6,890,346 B2 | 5/2005 | Ganz et al. |
| 6,902,535 B2 | 6/2005 | Eberhart et al. |
| 6,923,754 B2 | 8/2005 | Lubock |
| 6,931,286 B2 | 8/2005 | Sigg et al. |
| 6,939,299 B1 | 9/2005 | Petersen et al. |
| 6,942,680 B2 | 9/2005 | Grayzel et al. |
| 6,958,052 B1 | 10/2005 | Charlton |
| 7,001,419 B2 | 2/2006 | DiCaprio et al. |
| 7,016,735 B2 | 3/2006 | Imran et al. |
| 7,020,531 B1 | 3/2006 | Colliou et al. |
| 7,033,373 B2 | 4/2006 | de la Torre et al. |
| 7,056,305 B2 | 6/2006 | Garza Alvarez |
| 7,076,305 B2 | 7/2006 | Imran et al. |
| 7,081,125 B2 | 7/2006 | Edwards et al. |
| 7,131,945 B2 | 11/2006 | Fink et al. |
| 7,483,746 B2 | 1/2009 | Lee et al. |
| 7,625,355 B2 | 12/2009 | Yu |
| 7,749,254 B2 | 7/2010 | Sobelman et al. |
| 7,828,749 B2 | 11/2010 | Douglas et al. |
| 7,931,693 B2 | 4/2011 | Binmoeller et al. |
| 8,083,757 B2 | 12/2011 | Gannoe et al. |
| 8,556,925 B2 | 10/2013 | Makower et al. |
| 8,840,952 B2 | 9/2014 | Ashby et al. |
| 8,894,568 B2 | 11/2014 | Pecor et al. |
| 9,050,174 B2 | 6/2015 | Pecor et al. |
| 9,149,611 B2 | 10/2015 | Bouasaysy et al. |
| 2001/0022988 A1 | 9/2001 | Schwarz et al. |
| 2001/0037127 A1 | 11/2001 | De Hoyos Garza |
| 2002/0055757 A1 | 5/2002 | Torre et al. |
| 2002/0107515 A1* | 8/2002 | Edwards et al. ............ 606/41 |
| 2002/0161388 A1 | 10/2002 | Samuels et al. |
| 2002/0173804 A1 | 11/2002 | Rousseau |
| 2003/0105800 A1 | 6/2003 | Cullen |
| 2003/0114878 A1 | 6/2003 | Diederich et al. |
| 2003/0171768 A1 | 9/2003 | McGhan |
| 2003/0187390 A1 | 10/2003 | Bates et al. |
| 2004/0044354 A1 | 3/2004 | Gannoe et al. |
| 2004/0059289 A1 | 3/2004 | Garza Alvarez |
| 2004/0059290 A1 | 3/2004 | Palasis |
| 2004/0073162 A1 | 4/2004 | Bleam et al. |
| 2004/0087902 A1 | 5/2004 | Richter |
| 2004/0093058 A1 | 5/2004 | Cottone et al. |
| 2004/0106899 A1 | 6/2004 | McMichael et al. |
| 2004/0116897 A1 | 6/2004 | Aboul-Hosn |
| 2004/0127915 A1 | 7/2004 | Fleenor et al. |
| 2004/0186502 A1 | 9/2004 | Sampson et al. |
| 2004/0220665 A1 | 11/2004 | Hossainy et al. |
| 2004/0236280 A1 | 11/2004 | Rice et al. |
| 2004/0236361 A1 | 11/2004 | Sakurai |
| 2004/0254600 A1 | 12/2004 | Zarbatany et al. |
| 2005/0027283 A1 | 2/2005 | Richard et al. |
| 2005/0027313 A1* | 2/2005 | Shaker ...................... 606/197 |
| 2005/0038415 A1 | 2/2005 | Rohr et al. |
| 2005/0055039 A1 | 3/2005 | Burnett et al. |
| 2005/0059990 A1 | 3/2005 | Ayala et al. |
| 2005/0075624 A1 | 4/2005 | Miesel |
| 2005/0085792 A1 | 4/2005 | Gershowitz |
| 2005/0119674 A1 | 6/2005 | Gingras |
| 2005/0131442 A1 | 6/2005 | Yachia et al. |
| 2005/0143784 A1 | 6/2005 | Imran |
| 2005/0159769 A1 | 7/2005 | Alverdy |
| 2005/0177103 A1 | 8/2005 | Hunter et al. |
| 2005/0192615 A1 | 9/2005 | Torre et al. |
| 2005/0267595 A1 | 12/2005 | Chen et al. |
| 2005/0267596 A1 | 12/2005 | Chen et al. |
| 2005/0273060 A1* | 12/2005 | Levy et al. .................. 604/192 |
| 2006/0058829 A1 | 3/2006 | Sampson et al. |
| 2006/0178691 A1 | 8/2006 | Binmoeller |
| 2006/0184112 A1 | 8/2006 | Horn et al. |
| 2006/0259020 A1 | 11/2006 | Sharratt |
| 2007/0016262 A1 | 1/2007 | Gross et al. |
| 2007/0078476 A1 | 4/2007 | Hull et al. |
| 2007/0083224 A1 | 4/2007 | Hively |
| 2007/0093728 A1 | 4/2007 | Douglas et al. |
| 2007/0100367 A1 | 5/2007 | Quijano et al. |
| 2007/0100368 A1 | 5/2007 | Quijano et al. |
| 2007/0100369 A1* | 5/2007 | Cragg et al. .................. 606/192 |
| 2007/0135829 A1 | 6/2007 | Paganon et al. |
| 2007/0142770 A1 | 6/2007 | Rioux et al. |
| 2007/0149994 A1 | 6/2007 | Sosnowski et al. |
| 2007/0173881 A1 | 7/2007 | Birk et al. |
| 2007/0233161 A1* | 10/2007 | Weller et al. ................. 606/139 |
| 2007/0250020 A1 | 10/2007 | Kim et al. |
| 2007/0265369 A1 | 11/2007 | Muratoglu et al. |
| 2007/0265598 A1 | 11/2007 | Karasik |
| 2007/0288033 A1 | 12/2007 | Murature et al. |
| 2008/0058887 A1 | 3/2008 | Griffin et al. |
| 2008/0082056 A1 | 4/2008 | Mauch et al. |
| 2008/0085887 A1 | 4/2008 | Didiuk et al. |
| 2008/0097513 A1 | 4/2008 | Kaji et al. |
| 2008/0119729 A1 | 5/2008 | Copa et al. |
| 2008/0172079 A1* | 7/2008 | Birk .............................. 606/192 |
| 2008/0190363 A1 | 8/2008 | Chen et al. |
| 2008/0208135 A1 | 8/2008 | Annunziata et al. |

(56) References Cited

U.S. PATENT DOCUMENTS

| | | | |
|---|---|---|---|
| 2008/0208241 | A1 | 8/2008 | Weiner et al. |
| 2008/0233167 | A1 | 9/2008 | Li et al. |
| 2008/0243071 | A1 | 10/2008 | Quijano et al. |
| 2008/0243166 | A1 | 10/2008 | Paganon et al. |
| 2008/0255601 | A1 | 10/2008 | Birk |
| 2008/0312679 | A1 | 12/2008 | Hardert et al. |
| 2008/0319471 | A1 | 12/2008 | Sosnowski et al. |
| 2009/0048624 | A1 | 2/2009 | Alverdy |
| 2009/0259236 | A2 | 10/2009 | Burnett et al. |
| 2009/0275973 | A1 | 11/2009 | Chen et al. |
| 2009/0287231 | A1 | 11/2009 | Brooks et al. |
| 2010/0023047 | A1 | 1/2010 | Simpson |
| 2010/0130998 | A1 | 5/2010 | Alverdy |
| 2010/0234853 | A1 | 9/2010 | Pecor et al. |
| 2010/0243135 | A1 | 9/2010 | Pepper et al. |
| 2010/0251837 | A1 | 10/2010 | Bouasaysy et al. |
| 2011/0172767 | A1 | 7/2011 | Rathi et al. |
| 2012/0191126 | A1 | 7/2012 | Pecor et al. |
| 2012/0271336 | A1 | 10/2012 | Hamman et al. |
| 2012/0271338 | A1 | 10/2012 | Bouasaysy et al. |
| 2012/0289992 | A1 | 11/2012 | Quijano et al. |
| 2013/0035710 | A1 | 2/2013 | Bouasaysy et al. |
| 2013/0053880 | A1 | 2/2013 | Bouasaysy et al. |
| 2013/0102876 | A1 | 4/2013 | Limon et al. |
| 2013/0261654 | A1 | 10/2013 | Bouasaysy et al. |
| 2013/0296914 | A1 | 11/2013 | Quijano et al. |
| 2014/0031850 | A1 | 1/2014 | Bouasaysy et al. |
| 2014/0257358 | A1 | 9/2014 | Alverdy et al. |
| 2014/0371775 | A1 | 12/2014 | Ashby et al. |
| 2015/0216529 | A1 | 8/2015 | Kwok et al. |
| 2015/0238342 | A1 | 8/2015 | Sosnowski et al. |
| 2015/0265811 | A1 | 9/2015 | Pecor |

FOREIGN PATENT DOCUMENTS

| | | | |
|---|---|---|---|
| EP | 0457456 A1 | 11/1991 | |
| EP | 0485903 A2 | 5/1992 | |
| EP | 1781183 | 5/2007 | |
| FR | 2862525 A1 | 5/2005 | |
| FR | 2892297 | 4/2007 | |
| GB | 2090747 A | 7/1982 | |
| GB | 2139902 A | 11/1984 | |
| JP | S57168674 | 10/1982 | |
| JP | S6415063 | 1/1989 | |
| JP | H091872 | 4/1989 | |
| JP | H08322943 | 12/1996 | |
| JP | 2001128985 | 5/2001 | |
| JP | 2006333888 | 12/2006 | |
| WO | 9000369 A1 | 1/1990 | |
| WO | 9925418 A1 | 5/1999 | |
| WO | WO-0141700 | 6/2001 | |
| WO | WO-0166166 A2 | 9/2001 | |
| WO | WO0240081 | 5/2002 | |
| WO | WO-2006035446 A2 | 4/2006 | |
| WO | WO-2006056944 A1 | 6/2006 | |
| WO | WO-2006/128978 A1 | 12/2006 | |
| WO | WO-2007027812 A2 | 3/2007 | |
| WO | WO-2007053556 A1 | 5/2007 | |
| WO | WO-2007053706 A1 | 5/2007 | |
| WO | WO-2007053707 A1 | 5/2007 | |
| WO | WO-2007075810 A1 | 7/2007 | |
| WO | WO-2008042819 A2 | 4/2008 | |
| WO | WO-2008121831 A1 | 10/2008 | |
| WO | WO-2009112786 A2 | 9/2009 | |
| WO | WO-2010048021 | 4/2010 | |
| WO | WO-2010115161 A2 | 10/2010 | |
| WO | WO-2011011629 A2 | 1/2011 | |
| WO | WO-2011011741 A2 | 1/2011 | |
| WO | WO-2011011743 A2 | 1/2011 | |
| WO | WO-2011024077 A2 | 3/2011 | |
| WO | WO-2011038270 A2 | 3/2011 | |
| WO | WO-2011097637 A1 | 8/2011 | |
| WO | WO-2011127205 A1 | 10/2011 | |
| WO | WO-2012048226 A1 | 4/2012 | |

OTHER PUBLICATIONS

International Search Report; International Application No. PCT/US2011/024077; Applicant: ReShape Medical, Inc., Mailing Date Apr. 6, 2011, 12 pages.

International Search Report; International Application No. PCT/US2010/042948; Applicant: ReShape Medical, Inc., Mailing Date Apr. 1, 2011, 11 pages.

International Search Report; International Application No. PCT/US2010/043136; Applicant: ReShape Medical, Inc., Mailing Date Apr. 12, 2011, 9 pages.

International Search Report; International Application No. PCT/US2010/043134; Applicant: ReShape Medical, Inc., Mailing Date Apr. 27, 2011, 12 pages.

International Search Report; International Application No. PCT/US2011/0426233; Applicant: ReShape Medical, Inc., Mailing Date Apr. 26, 2011, 9 pages.

"ReShape Inflatable Gastric Balloon Going on Trial as Weight Loss Option," MedGadget: Internet Journal of Emerging Medical Technologies. Feb. 4, 2010. (5 pages).

Wahlen Ch et al. "The BioEnterics Intragastric Balloon: How to use it" Obesity Surgery 2001; 11:524-527.

Patient Information "Living with the BIB" by INAMED Health (2004).

International Search Report; International Application No. PCT/US2008/058677, Applicant: ReShape Medical et al., Mailing Date Aug. 21, 2008, 12 pages.

International Search Report; International Application No. PCT/US2006/042710, Applicant: Abdominus, Inc. et al., Mailing Date Mar. 15, 2007, 9 pages.

International Search Report; International Application No. PCT/US2006/048647, Applicant: Abdominus, Inc. et al., Mailing Date May 22, 2007, 12 pages.

International Search Report; International Application No. PCT/US2008/068058, Applicant: ReShape Medical, Inc. et al, Mailing Date Nov. 19, 2008, 11 pages.

International Search Report; International Application No. PCT/US2006/042711, Applicant: Abdominus, Inc. et al, Mailing Date Mar. 16, 2007, 9 pages.

Supplementary European Search Report for EP 03726447.0, mailed Mar. 1, 2006.

International Search Report; International Application No. PCT/US2003/012782, Applicant: Applied Medical Resources Corporation, Mailing Date Oct. 28, 2003, 7 pages.

International Search Report; International Application No. PCT/US2006/042336, Applicant: Abdominus, Inc., Mailing Date Mar. 14, 2007, 9 pages.

International Search Report; International Application No. PCT/US2010/029865, Applicant: ReShape Medical, Inc., Mailing Date Jan. 5, 2011, 9 pages.

Final Office Action; U.S. Appl. No. 11/694,536, Mailing Date Mar. 11, 2011, 13 pages.

Final Office Action; U.S. Appl. No. 11/768,152, Mailing Date Jan. 19, 2011, 13 pages.

Extended European Search Report; Application No. EP6827098.3, Applicant: Reshape Medical Corporation, mailed on Aug. 25, 2014, 3 pages.

Extended European Search Report; Application No. EP6827314.3, Applicant: ReShape Medical Corporation, mailed Aug. 1, 2014, 3 pages.

Extended European Search Report; Application No. EP6827313.5, Applicant: ReShape Medical Corporation, mailed Jul. 30, 2014, 5 pages.

Extended European Search Report; Application No. EP6847847.8, Applicant: ReShape Medical Corporation, mailed Aug. 14, 2014, 5 pages.

Final Office Action: U.S. Appl. No. 13/858,767, mailed on May 30, 2014, 12 pages.

Non-Final Office Action; U.S. Appl. No. 13/386,638, mailed on Jun. 27, 2014, 12 pages.

(56) References Cited

OTHER PUBLICATIONS

International Search Report; International Application No. PCT/US1155373, Applicant: Reshape Medical, Inc., dated: Jan. 20, 2012, 7 pages.
International Search Report; International Application No. PCT/US2010/050260; Applicant: ReShape Medical, Inc., Mailing Date: Jun. 17, 2011, 9 pages.
International Search Report; International Application No. PCT/US2011/031463; Applicant: ReShape Medical, Inc., Mailing Date: Jun. 27, 2011, 10 pages.
Non-Final Office Action; U.S. Appl. No. 11/263,302; dated: Oct. 9, 2012, 6 pages.
Non-Final Office Action; U.S. Appl. No. 11/694,536; dated: Oct. 26, 2011, 13 pages.
Non-Final Office Action; U.S. Appl. No. 12/625,473; dated Jul. 12, 2012; 10 pages.
Non-Final Office Action; U.S. Appl. No. 12/625,473; dated Oct. 24, 2011, 18 pages.
Non-Final Office Action; U.S. Appl. No. 12/723,545; dated Feb. 29, 2012, 10 pages.
Non-Final Office Action; U.S Appl. No. 12/753,751; dated Oct. 5, 2012, 8 pages.
European Supplementary Search Report; EP Application No. 10802994.3, Applicant: ReShape Medical, Inc., mailed Jun. 28, 2013, 8 pgs.
European Supplementary Search Report; EP Application No. 10802918.2, Applicant: ReShape Medical, Inc., mailed Jun. 5, 2013, 6 pgs.
Extended European Search Report; Application No. EP11748141.6, Applicant: Reshape Medical, Inc., mailed Feb. 25, 2014, 6 pages.
Extended European Search Report; Application EP11740536.5, Applicant: ReShape Medical, Inc., mailed Jul. 3, 2014, 8 pages.
Extended European Search Report; Application EP11831683.5, Applicant: Reshape Medical, Inc., mailed Jul. 3, 2014, 8 pages.
Final Office Action: U.S. Appl. No. 13/556,0-32, mailed on Jan. 28, 2014, 8 pages.
Non-Final Office Action: U.S. Appl. No. 13/386,650, mailed on Jun. 3, 2014, 15 pages.
Notice of Allowance; U.S. Appl. No. 12/753,803, dated May 13, 2014, 18 pages.
Ostrovsky, ReShape Inflatable Gastric Balloon going on Trial as Weight Loss Option: http://www.medgadget.com/2010/reshape_inflatable_gastric_balloon_system_going_on_trial_as_wieight_loss_option.html Feb. 4, 2010, retrieved on Feb. 10, 2013.
Final Office Action; U.S. Appl. No. 13/858,767, Mailing Date May 22, 2013, 12 pages.
Extended European Search Report; Application No. EP11766679.2; Applicant: Reshape Medical, Inc., mailed Dec. 12, 2013, 6 pages.
Cronin et al., "Normal small bowel wall characteristics on MR enterography," European Journal of Radiology 74(2)207-211, Aug. 2010.
Canadian 2nd Office Action Application No. 2680124, Applicant: ReShape Medical, Inc., mailed Jul. 9, 2015, 3 pages.
European Examination Report; Application No. 06827313.5, Applicant: ReShape Medical Inc., mailed Jul. 13, 2015, 5 pages.
European Examination Report; Application No. 06847847.8, Applicant: ReShape Medical Inc., mailed Jul. 13, 2015, 4 pages.
Japanese Office Action; Application No. 2013-532976; Applicant: ReShape Medical, Inc., mailed Jun. 26, 2015, 10 pages.
Canadian Office Action: Application No. CA 2680124, Applicant: Reshape Medical Corporation, mailed Nov. 4, 2014, 3 pages.
Canadian Office Action; Application No. 2,691,530, mailed Dec. 18, 2014, 4 pages.
Canadian Office Action; Application No. CA 2638163, Applicant: Reshape Medical Corporation, mailed Mar. 10, 2015, 4 pages.
Canadian Office Action; Application No. CA 2638988, Applicant Reshape Medical Corporation, mailed Dec. 22, 2014 3 pages.
Canadian Office Action; Application No. CA 2638988, Applicant Reshape Medical Corporation, mailed Mar. 6, 2014, 4 pages.
Canadian Office Action; Application No. CA 2638989, Applicant: Reshape Medical Corporation, mailed May 22, 2013 3 pages.
Canadian Office Action; Application No. CA 2640554, Applicant: Reshape Medical Corporation, mailed May 27, 2013, 2 pages.
Canadian Office Action; Application No. CA2484838, Applicant: Reshape Medical, Inc., mailed Nov. 13, 2009, 3 pages.
Canadian Office Action; Application No. CA2484838, Applicant: Reshape Medical, Inc., mailed Sep. 24, 2010, 3 pages.
Canadian Office Action; Application No. CA2638163, Applicant: Reshape Medical Corporation, mailed Jul. 17, 2013, 2 pages.
Canadian Office Action; Application No. CA2638988, Applicant: Reshape Medical Corporation, mailed May 28, 2013, 3 pages.
Canadian Office Action; Application No. CA2780085, Applicant: Reshape Medical, Inc., mailed Jul. 23, 2012, 2 pages.
European Examination Report; Application No. 03726447.0, Applicant: Applied Medical Resources Corporation: Oct. 26, 2007, 4 pages.
European Examination Report; Application No. EP108002918.2, Applicant: Reshape Medical Inc., mailed Dec. 17, 2014, 5 pages.
European Examination Report; Application No. EP108029943, Applicant: Reshape Medical Inc., mailed Dec. 18, 2014, 4 pages.
European Examination Reported; Application No. 08771842.5, May 7, 2015, 5 pages.
European Supplementary Search Report; Application No. 08771842.5, Apr. 24, 2015, 3 pages.
Extended European Search Report; Application No. 08732989.2, Applicant: Reshape Medical, Inc., mailed Oct. 16, 2014, 7 pages.
Japanese Final Office Action; Application No. JP2013-043712, mailed Nov. 15, 2013, 5 pages.
Japanese Office Action; Application No. 2013-142327, mailed May 29, 2014, 4 pages.
Japanese Office Action; Application No. 2014-52972; mailed Feb. 25, 2015, 7 pages.
Japanese Office Action; Application No. JP2010-501261, mailed Sep. 7, 2012, 10 pages.
Japanese Office Action; Application No. JP2010-515040, mailed Jan. 7, 2013, 18 pages.
Japanese Office Action; Application No. JP2012-503759, mailed Mar. 24, 2014, 5 pages.
Japanese Office Action; Application No. JP2013-43712, mailed Jan. 8, 2015, 8 pages.
Japanese Office Action; Application. No. JP2013-043712, mailed Apr. 22, 2013, 5 pages.
Gray, Henry. Anatomy of the Human Body. Philadelphia: Lea & Febiger, 1918. Section XI Splanchnology, 2g. The Small Intestine. Bartleby.com, 2000. Web. URL: www.bartleby.com/107/248.html. Accessed: Oct. 26, 2015. 12 pages.
Partial Supplementary European Search Report for European Application No. 11740535.7, Applicant: ReShape Medical, Inc., mailed Oct. 20, 2015, 7 pages.
Final Office Action for Japanese Application No. 2014-52972, Applicant: ReShape Medical, Inc., mailed on Oct. 9, 2015, 8 pages.

\* cited by examiner

GASTRIC SPACE FILLER DEVICE, DELIVERY SYSTEM, AND RELATED METHODS

CROSS-REFERENCE TO RELATED APPLICATION(S)

The present application is a continuation of U.S. patent application Ser. No. 11/768,152, filed Jun. 25, 2007, the disclosure of which is incorporated herein by reference in its entirety.

RELATED REFERENCES

This application incorporates by reference in their entirety each of the following applications:
(a) U.S. patent application Ser. No. 11/694,536, filed Mar. 30, 2007;
(b) PCT/US06/42336, filed Oct. 31, 2006;
(c) PCT/US06/42711, filed Oct. 31, 2006;
(d) PCT/US06/42710, filed Oct. 31, 2006; and
(e) PCT/US06/48647, filed Dec. 20, 2006.

BACKGROUND

1. Field

This disclosure relates to implantable weight control devices. More particularly, this disclosure relates to a gastric space filler device which is retrievably implantable in a patient, an improved device and method for delivery of a gastric space filler device, and a method and device for retaining fluid in a gastric space filler device, among other things.

2. General Background

Gastric space fillers used for achieving loss of weight in extremely obese persons have been known in the art. Some gastric space fillers utilized for this purpose function on the principle that an empty bag or space filler is placed into the stomach through the esophagus. Thereafter, the bag or space filler is fully or partially filled with a suitable insufflation fluid, such as saline solution, through a filler tube or catheter which is inserted into the stomach through the mouth or the nose. The space filler occupies space in the stomach thereby leaving less room available for food and creating a feeling of satiety for the obese person. Clinical experience has shown that, for many obese patients, reducing the size of the gastric compartment with gastric space fillers significantly helps to control appetite and accomplish weight loss. The present disclosure is directed to a device which non-operatively reduces the size of the gastric compartment and which is easily removed. Artisans shall readily appreciate that emergency operative morbidity rates and co-morbidity statistics relating to such devices which have migrated beyond the stomach underscore the need for an effective medical device that can be removed.

SUMMARY

According to features of the present disclosure, a gastric space filler device and methods effective for reducing stomach volume are disclosed. A gastric space filler comprising at least one inflatable space filler and a sleeve to prevent leakage out of the gastric space filler device is disclosed. The gastric space filler device may be inflated with an insufflation fluid and with mineral oil, which further has the effect of reducing leakage. Delivery systems and methods for inserting a gastric space filler device into a patient are also disclosed. Sheaths and methods for covering a gastric space filler device during delivery into a patient are also disclosed.

According to embodiments of the instant teachings, there is disclosed a gastric space filler device comprising a space filler, an opening to inflate the space filler, and a sleeve that is configured to receive mineral oil between the sleeve and the opening. According to at least one embodiment, the sleeve is disposed between the opening and the outer periphery of the space filler. According to at least one embodiment, the sleeve allows fluid to enter the space filler during inflation, but does not allow fluid to exit the space filler when mineral oil is received between the sleeve and the opening.

According to embodiments of the instant teachings, there is disclosed a gastric space filler device comprising a space filler and a sheath, wherein the sheath at least partially covers the space filler. According to at least one embodiment, the sheath is secured around the space filler with a stitch that can be released by pulling on the stitch. According to at least one embodiment, the sheath automatically uncovers the space filler as the space filler is inflated.

According to embodiments of the instant teachings, there is disclosed a delivery system comprising a delivery lumen, a barb configured for coupling with an infusing lumen of a gastric space filler device, and a docking clip configured for securely attaching the delivery system to the gastric space filler device. According to at least one embodiment, the delivery system contains a handle that, when removed from the infusing lumen, pulls a stitch to release a space filler and simultaneously uncovers a luer for infusing a fluid into the gastric space filler device.

According to embodiments of the instant teachings, there is disclosed a method for treating obesity challenged patients comprising providing a gastric space filler device comprising a space filler, an opening to inflate the space filler with a fluid, and a sleeve disposed between the opening and an outer periphery of the space filler; allowing the fluid to enter the space filler through the opening; and preventing the fluid from exiting the space filler through the opening.

According to embodiments of the instant teachings, there is disclosed a method for emplacing a gastric space filler device in a patient comprising providing a delivery system attached to a gastric space filler device comprising a space filler; covering at least part of the space filler with a sheath; and delivering the delivery system and the gastric space filler device through an esophagus into a stomach of a patient.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Figure 1:
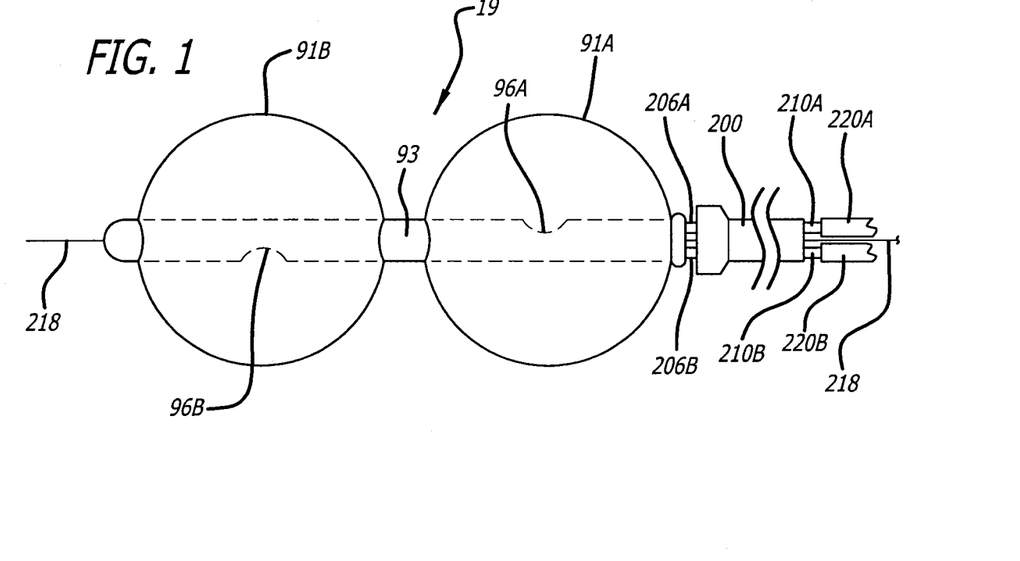
FIG. 1 shows an embodiment of a gastric space filler device and delivery system.

According to an embodiment as schematically depicted in FIG. 1, gastric space filler device 19 comprises proximal space filler 91A, distal space filler 91B, and infusing member 93. Proximal space filler 91A is filled with an insufflation fluid through proximal opening 96A of infusing member 93, and distal space filler 91B is filled with fluid from distal opening 96B of infusing member 93. Delivery system 200 infuses and expands gastric space filler device 19.

According to an illustrative embodiment, proximal space filler 91A and distal space filler 91B are spaced apart and secured to each other by infusing member 93. According to an illustrative embodiment, the distance between the two space fillers is between at least about 10 to approximately 40 mm. The overall axial length of gastric space filler device 19 is between about 100 and about 300 mm. According to an illustrative embodiment, infusing member 93 may be made of semi-flexible or flexible material. The semi-flexible material may be selected from space filler-compatible polymer, such as, polyethylene, polystyrene, polyurethane, silicone, fluoropolymer, and co-polymers thereof.

According to an illustrative embodiment, the longitudinal length of proximal space filler 91A is between about 70 and about 80 mm, preferably about 75 mm. Proximal space filler 91A may be expanded to a space volume of between about 100 and about 600 cc. In an embodiment, the longitudinal length of distal space filler 91B is between about 60 and about 70 mm, preferably about 65 mm.

Distal space filler 91B may be expanded to a space volume of between about 100 and about 400 cc. According to a further embodiment, a radial diameter of proximal space filler 91A may be expanded to a diameter between about 40 and about 60 mm, and a radial diameter of distal space filler 91B may be expanded to a diameter between about 20 and about 40 mm. According to an illustrative embodiment, proximal space filler 91A is substantially larger than distal space filler 91B in gastric space filler device 19 to take the advantage of the restricted space at the entrance region of the stomach and to create a better feeling of satiety for the patient. According to an illustrative embodiment, the thickness of proximal space filler 91A and distal space filler 91B is between about 0.2 and about 1.0 mm, effectively between about 0.3 to about 0.5 mm.

Figure 2A:
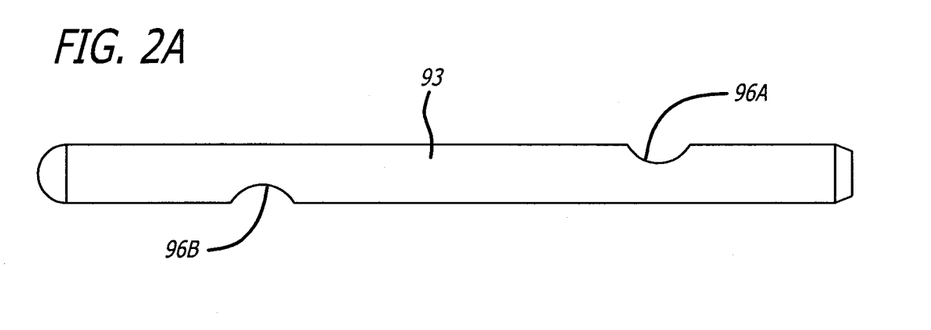
FIG. 2A shows an embodiment of an infusing member without proximal sleeve or distal sleeve.
Figure 2B:
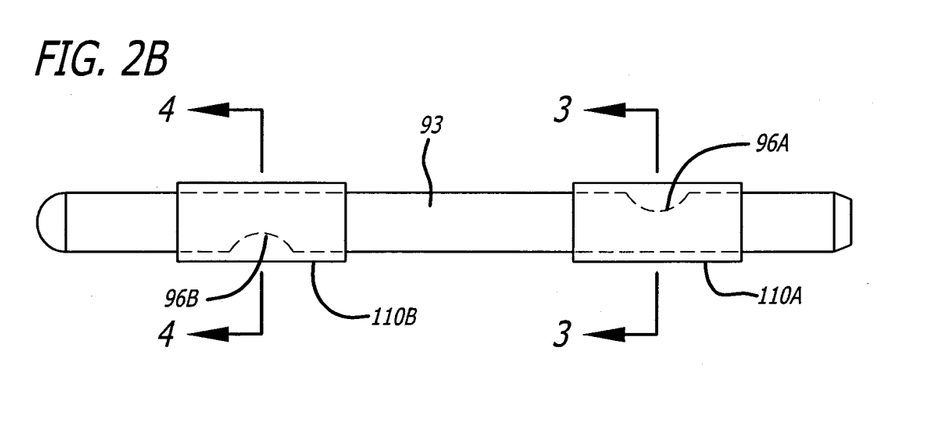
FIG. 2B shows an embodiment of an infusing member with a proximal sleeve and a distal sleeve.

According to an embodiment as depicted in FIG. 2B, infusing member 93 contains proximal sleeve 110A that wraps around infusing member 93 and covers proximal opening 96A, which connects proximal space filler 91A to proximal infusing lumen 94A. Infusing member 93 also contains distal sleeve 110B that wraps around infusing member 93 and covers distal opening 96B, which connects distal space filler 91B to distal infusing lumen 94B.

Figures 3, 4, 5, 6:
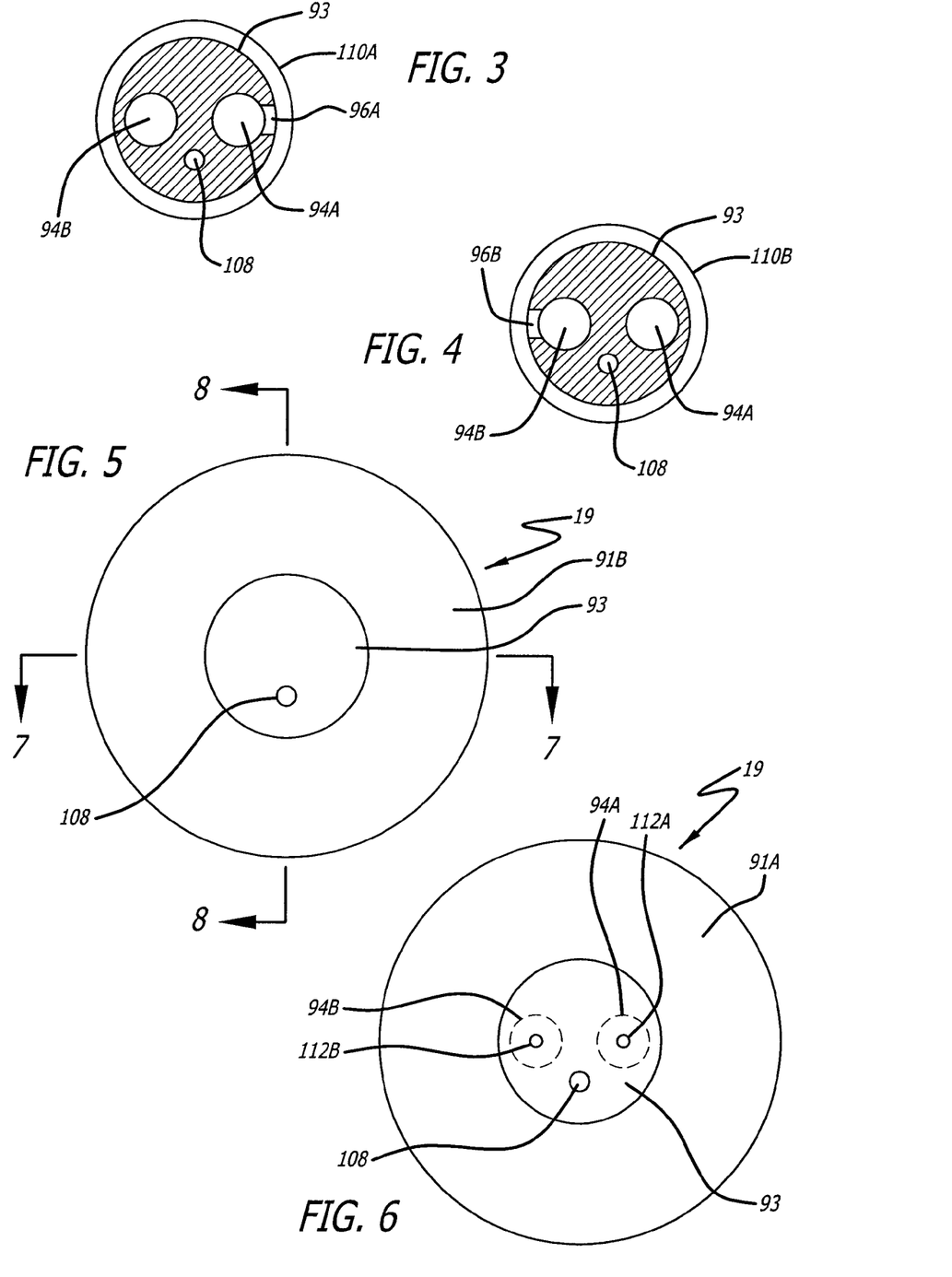
FIG. 3 shows a cross-sectional view of an embodiment of an infusing member, a proximal sleeve, and a proximal opening.
FIG. 4 shows a cross-sectional view of an embodiment of an infusing member, a distal sleeve, and a distal opening.
FIG. 5 shows a rear view of an embodiment of a gastric space filler device containing a distal space filler.
FIG. 6 shows a front view of an embodiment of a gastric space filler device containing a proximal space filler.

According to an embodiment as depicted in FIG. 3, proximal infusing lumen 94A of infusing member 93 has proximal opening 96A that provides fluid communication between infusing lumen 94A and proximal space filler 91A. According to an embodiment as depicted in FIG. 4, distal infusing lumen 94B of infusing member 93 has distal opening 96B that provides fluid communication between distal infusing lumen 94B and distal space filler 91B. Proximal space filler 91A and proximal infusing lumen 94A are not in fluid communication with either distal space filler 91B or distal infusing lumen 94B. According to an illustrative embodiment, infusing member 93 has an inner diameter of between about 1 and about 6 mm. According to an illustrative embodiment, proximal infusing lumen 94A is substantially larger than distal infusing lumen 94B.

According to an illustrative embodiment, proximal opening 96A connects proximal space filler 91A to proximal infusing lumen 94A. According to an illustrative embodiment, proximal sleeve 110A wraps around infusing member 93 and covers proximal opening 96A. Proximal sleeve 110A may be disposed between proximal opening 96A and outer periphery of proximal space filler 91A.

As proximal space filler 91A is being inflated, proximal sleeve 110A allows an insufflation fluid to enter proximal space filler 91A from proximal infusing lumen 94A through proximal opening 96A. According to an illustrative embodiment, proximal sleeve 110A allows an insufflation fluid to enter proximal space filler 91A by moving at least part of proximal sleeve 110A away from proximal opening 96A. According to an illustrative embodiment, at least part of proximal sleeve 110A is moved away from proximal opening 96A as a result of higher pressure outside proximal space filler 91A in relation to pressure inside proximal space filler 91A.

According to an illustrative embodiment, after proximal space filler 91A is inflated, proximal sleeve 110A is pressed against proximal opening 96A; thus proximal sleeve 110A does not allow fluid to exit proximal space filler 91A through proximal opening 96A. According to an illustrative embodiment, higher pressure inside proximal space filler 91A, relative to pressure outside proximal space filler 91A, presses proximal sleeve 110A against proximal opening 96A.

According to another embodiment, proximal sleeve 110A is not wrapped around infusing member 93, but is attached to infusing member 93 and is configured to move at least partially away from proximal opening 96A while proximal space filler 91A is being inflated and is also configured to block proximal opening 96A after proximal space filler 91A has been inflated.

According to an embodiment as depicted in FIG. 4, distal sleeve 110B covers distal opening 96B. Distal sleeve 110B allows inflation of distal space filler 91B through distal opening 96B and prevents deflation of distal space filler 91B through distal opening 96B while distal space filler 91B is inflated. Appropriate materials for proximal sleeve 110A or distal sleeve 110B include any elastomeric material, such as silicone.

According to an illustrative embodiment, an insufflation fluid, such as a saline solution, is used to inflate proximal space filler 91A or distal space filler 91B to a desired volume effective to fill the desired portion of a stomach of a patient and create the desired feeling of satiety. When proximal space filler 91A is inflated to this point, mineral oil is infused through proximal opening 96A and received between proximal sleeve 110A and proximal opening 96A. The mineral oil displaces the insufflation fluid in the area between proximal sleeve 110A and proximal opening 96A. Mineral oil between proximal sleeve 110A and proximal opening 96A has the effect of decreasing leakage of the insufflation fluid out of proximal space filler 91A through proximal opening 96A. According to an illustrative embodiment, an effective amount of mineral oil is the amount of mineral oil with volume equal to the volume of the insufflation fluid to be displaced by the mineral oil. According to an illustrative embodiment, mineral oil is received between distal sleeve 110B and distal opening 96B. Unexpectedly, this teaching substantially improves leakage and has yet to have been disclosed.

According to an embodiment as depicted in FIG. 6, proximal infusing lumen 94A contains proximal gate 112A, and distal infusing lumen 94B contains distal gate 112B, disposed at proximal end of infusing member 93. Proximal gate 112A prevents at least some of any fluid from traveling into or out of proximal infusing lumen 94A until proximal barb 206A is inserted through proximal gate 112A and into proximal infusing lumen 94A. Similarly, distal gate 112B prevents at least some of any fluid from traveling into or out of distal infusing lumen 94B until distal barb 206B is inserted through distal gate 112B and into distal infusing lumen 94B. Proximal gate 112A or distal gate 112B may be made of a flexible material that substantially covers proximal infusing lumen 94A or distal infusing lumen 94B and can be manipulated to allow insertion of proximal barb 206A or distal barb 206B.

Figure 7:
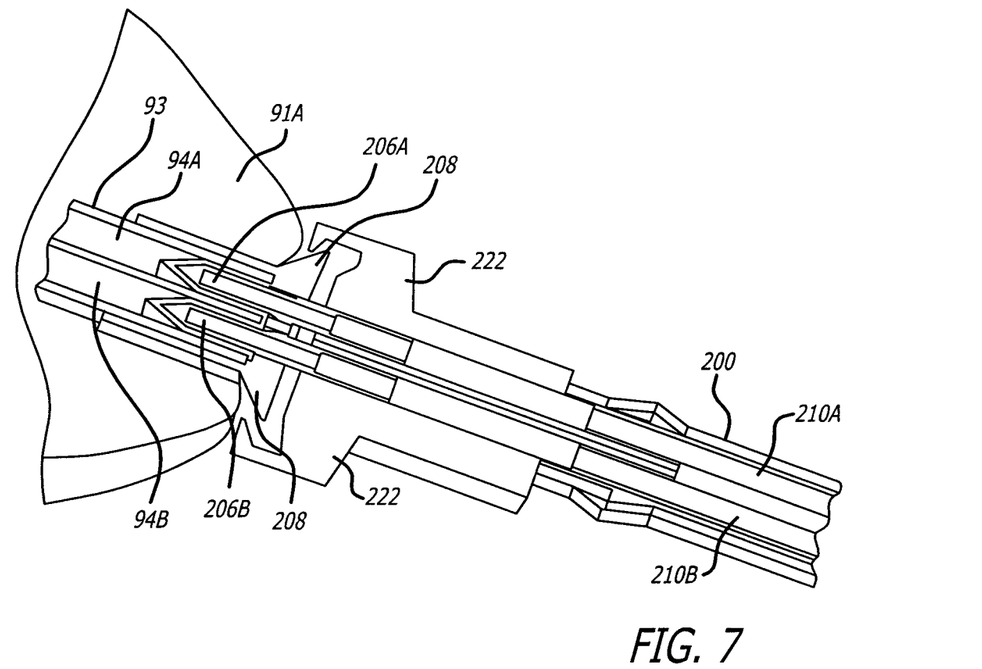
FIG. 7 shows a cross-sectional view of an embodiment of a gastric space filler device and a delivery system containing a proximal delivery lumen and a distal delivery lumen.

According to an embodiment as depicted in FIG. 7, after gastric space filler device 19 is delivered to the stomach of a patient, delivery system 200 is inserted through the mouth to securely couple with proximal end of gastric space filler device 19. According to another embodiment, delivery system 200 is securely coupled to gastric space filler device 19 before gastric space filler device 19 and delivery system 200 are delivered to the stomach of a patient. According to an illustrative embodiment, delivery system 200 may be coupled to gastric space filler device 19 by docking clip 222 of delivery system 200, which is configured to securely attach to docking notch 208 of gastric space filler device 19.

According to an illustrative embodiment, delivery system 200 contains proximal barb 206A and distal barb 206B. Proximal barb 206A is in fluid communication with proximal delivery lumen 210A, and distal barb 206B is in fluid communication with distal delivery lumen 210B. When delivery system 200 is securely coupled with proximal end of gastric space filler device 19, proximal barb 206A and distal barb 206B are at least partially inserted into proximal infusing lumen 94A and distal infusing lumen 94B, respectively.

Proximal space filler 91A may be inflated by delivering an insufflation fluid into proximal delivery lumen 210A, thereby delivering insufflation fluid through proximal barb 206A and into proximal infusing lumen 94A. Similarly, distal space filler 91B may be inflated by delivering an insufflation fluid into distal delivery lumen 210B, thereby delivering insufflation fluid through distal barb 206B and into the distal infusing lumen 94B.

Figure 8:
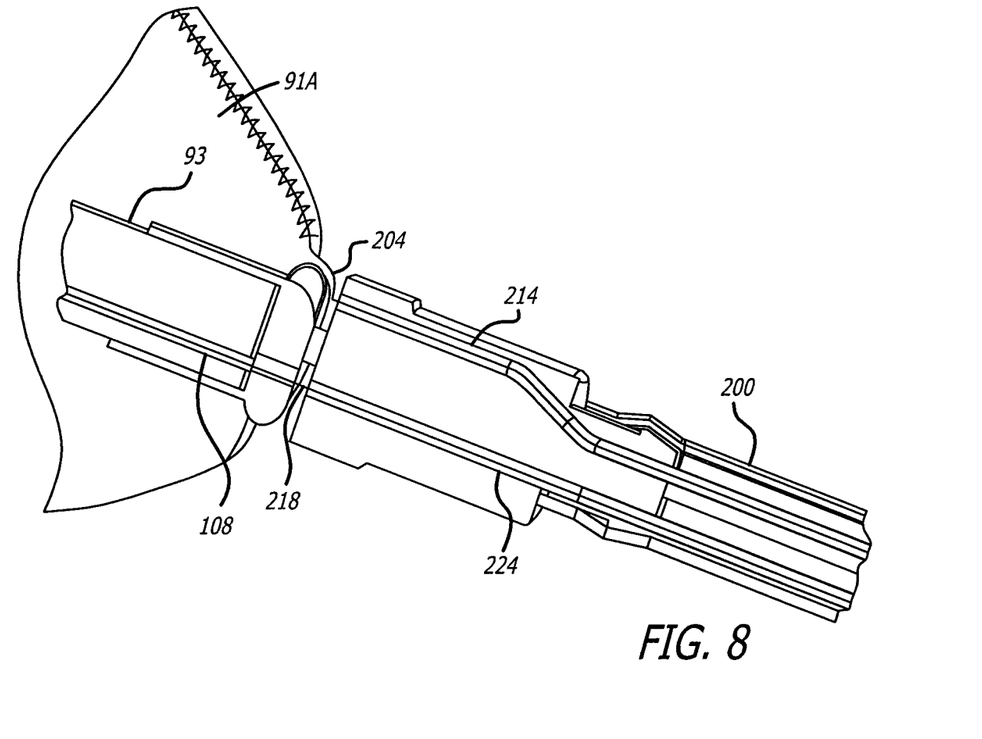
FIG. 8 shows a cross-sectional view of an embodiment of a gastric space filler device and a delivery system containing a stitch channel and a delivery guide wire channel.

According to an embodiment as depicted in FIG. 8, gastric space filler device 19 contains filler guide wire channel 108, and delivery system 200 contains delivery guide wire channel 224. According to an illustrative embodiment, guide wire 218 is laid along a path to be traveled by gastric space filler device 19 or delivery system 200. Guide wire 218 is then threaded through at least one of guide wire channel 108 of gastric space filler device 19 and delivery guide wire channel 224 of delivery system 200. Once threaded, gastric space filler device 19 or delivery system 200 may travel along guide wire 218.

Figure 9:
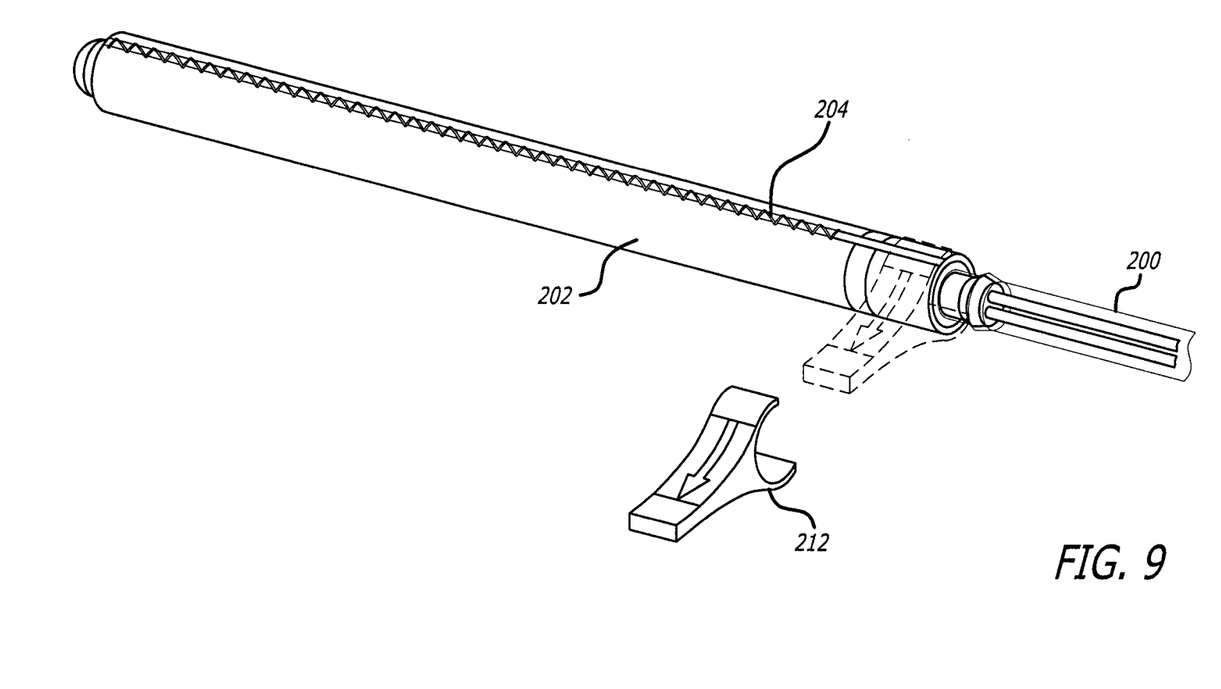
FIG. 9 shows an embodiment of a gastric space filler device and a delivery system containing a sheath, a stitch, and a sheath release clip.

According to an embodiment as depicted in FIG. 9, sheath 202 at least partially covers proximal space filler 91A and distal space filler 91B before or during insertion through an esophagus of a patient. Sheath 202 may be made from flexible or semi-flexible materials, including mesh fabric and silicone. According to an illustrative embodiment, sheath 202 is secured to gastric space filler device 19 by stitch 204. Various stitching patterns are known in the art. Stitch 204 may comprise an easily releasable stitching pattern, such as one that may be released by pulling on one end of stitch 204. When proximal space filler 91A or distal space filler 91B is ready to inflate, stitch 204 is removed.

According to an illustrative embodiment, at least part of stitch 204 is secured by sheath release clip 212 until gastric space filler device 19 is ready to be inserted into patient. Sheath release clip 212, while engaged, secures at least part of stitch 204, such that stitch 204 may not be released. When sheath release clip 212 is removed, stitch 204 is capable of being released.

According to an illustrative embodiment, at least part of stitch 204 is located inside stitch channel 214 of delivery system 200. This allows stitch 204 to be pulled away from gastric space filler device 19 without additional instruments. Where stitch 204 is released from sheath 202 by pulling on an end of stitch 204, stitch 204 may be released by pulling stitch 204 through stitch channel 214.

Figure 10A:
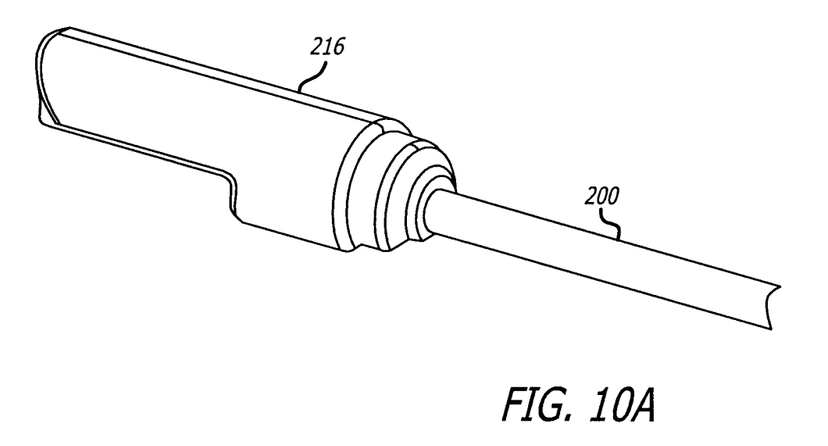
FIG. 10A shows an embodiment of a delivery system containing a handle.
Figure 10B:
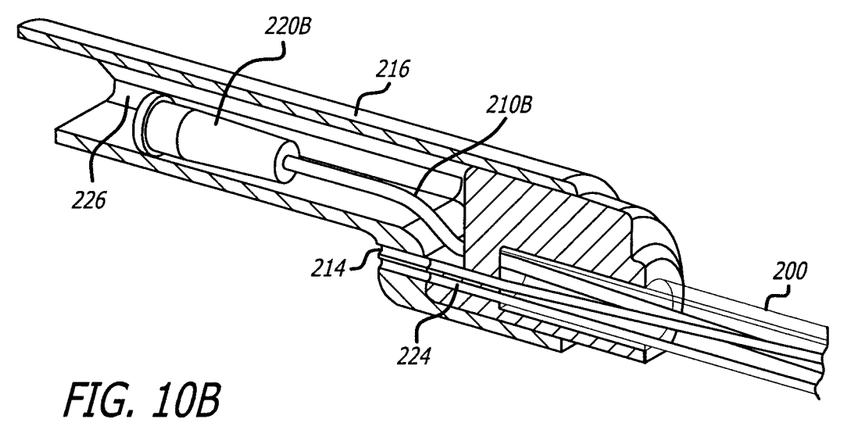
FIG. 10B shows a cross-sectional view of an embodiment of a delivery system containing a handle.

According to an embodiment as depicted in FIG. 10A, delivery system 200 may contain handle 216, which may be removably attached to delivery system 200. According to an embodiment as depicted in FIG. 10B, handle 216 contains inner compartment 226. Proximal luer 220A and distal luer 220B may be contained within inner compartment 226 while handle is attached to delivery system 200. While handle 216 is attached to delivery system 200, proximal luer 220A and distal luer 220B may not be accessed to infuse fluid into proximal space filler 91A or distal space filler 91B.

Figure 10C:
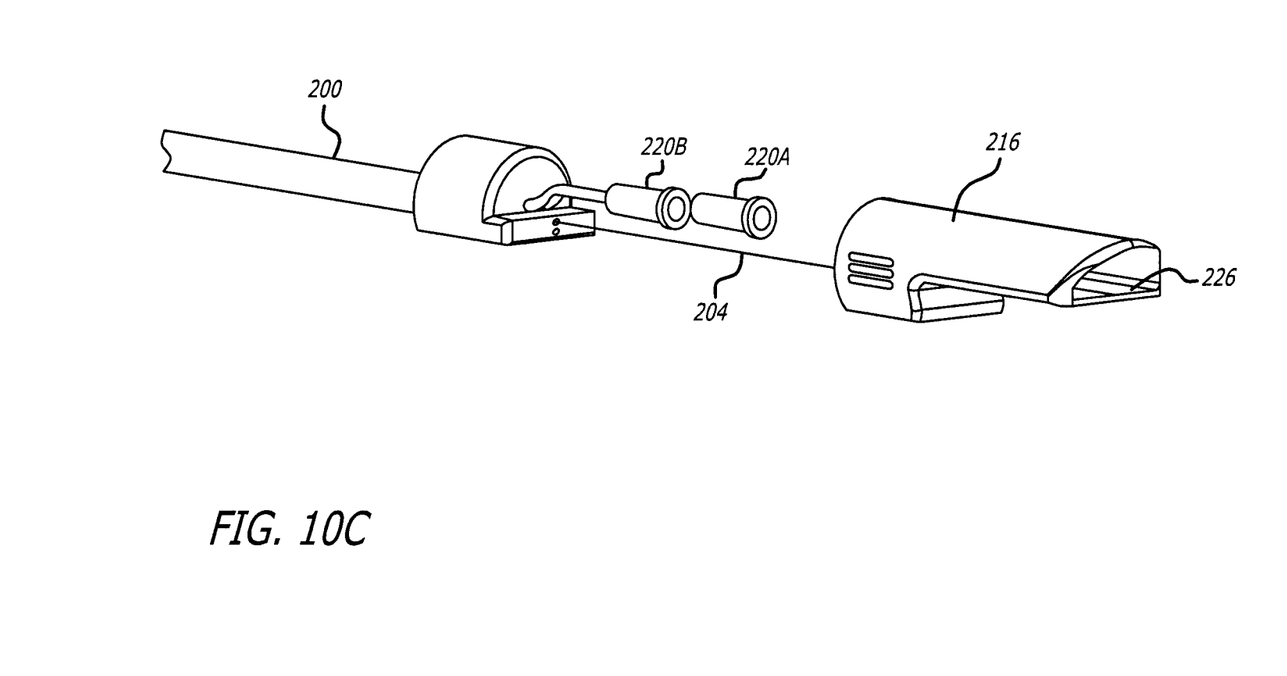
FIG. 10C shows an embodiment of a delivery system and a handle detached from delivery system.

According to an embodiment as depicted in FIG. 10C, stitch 204 may be attached to handle 216, such that when handle 216 is removed from delivery system 200, stitch 204 is pulled away from sheath 202, thereby releasing sheath 202 from covering proximal space filler 91A or distal space filler 91B. Likewise, removal of handle 216 exposes proximal luer 220A and distal luer 220B, such that proximal space filler 91A and distal space filler 91B can be infused only when handle 216 is removed. In this embodiment, proximal space filler 91A and distal space filler 91B cannot be inflated until sheath 202 is released.

Figure 11A:
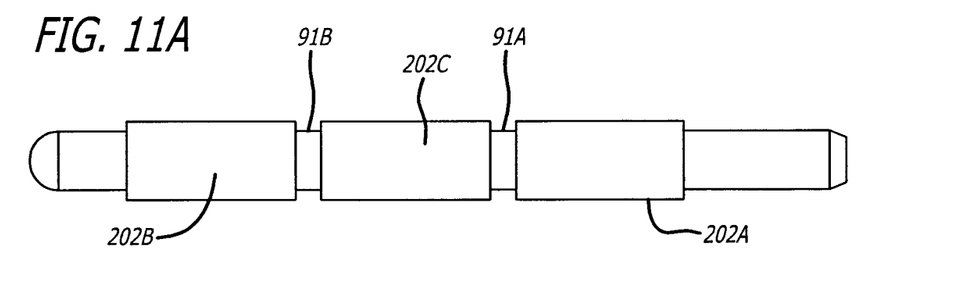
FIG. 11A shows an embodiment of a gastric space filler device and sheaths wherein a proximal space filler and a distal space filler are deflated.
Figure 11B:
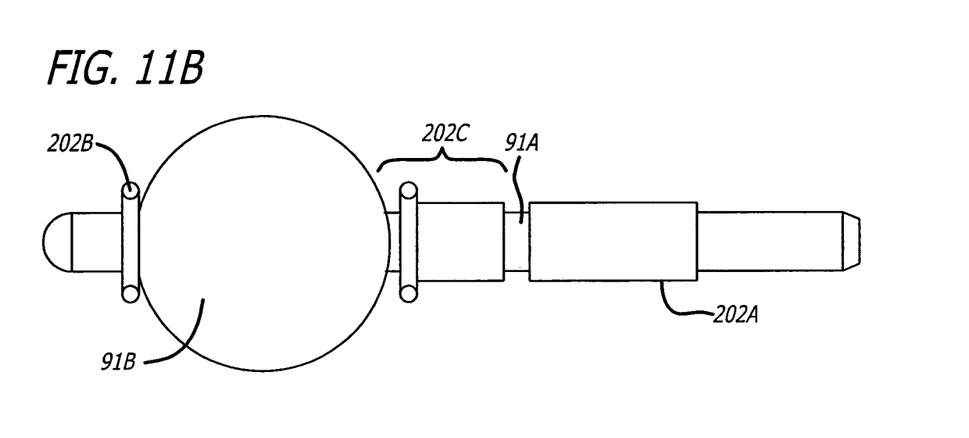
FIG. 11B shows an embodiment of a gastric space filler device, wherein a distal space filler is inflated.
Figure 11C:
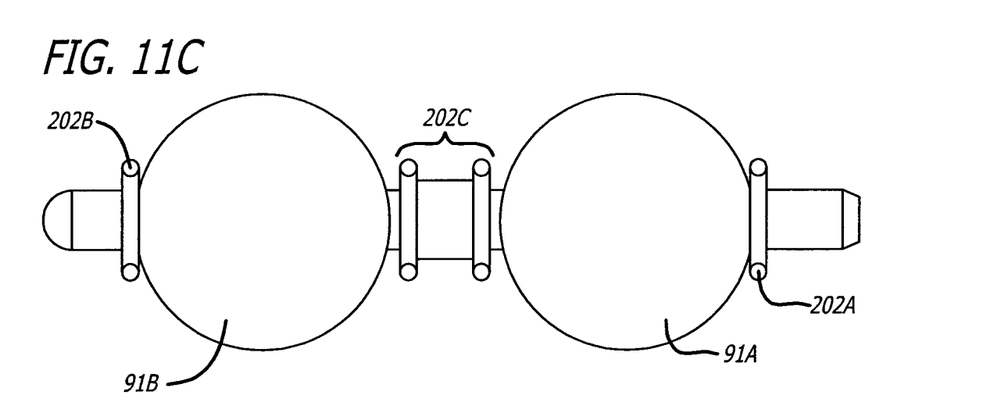
FIG. 11C shows an embodiment of a gastric space filler device, wherein a proximal space filler is inflated.

According to an embodiment as depicted in FIG. 11A, FIG. 11B, and FIG. 11C, gastric space filler device 19 is at least partially covered by three sheaths: proximal sheath 202A, central sheath 202C, and distal sheath 202B. Distal sheath 202B at least partially covers distal portion of distal space filler 91B, central sheath 202C at least partially covers proximal portion of distal space filler 91B and distal portion of proximal space filler 91A, and proximal sheath 202A at least partially covers proximal portion of proximal space filler 91A.

As distal space filler 91B is inflated, distal sheath 202B is rolled onto itself toward distal end of gastric space filler device 19 and distal portion of central sheath 202C is rolled onto itself toward center of gastric space filler device 19. As proximal space filler 91A is inflated, proximal sheath 202A is rolled onto itself toward proximal end of gastric space filler device 19, and proximal portion of central sheath 202C is rolled onto itself toward center of gastric space filler device 19. In an illustrative embodiment, as proximal space filler 91A is inflated, proximal sheath 202A is rolled onto itself toward delivery system 200 attached to proximal end of gastric space filler device 19, such that when proximal space filler 91A is inflated, proximal sheath 202A is rolled onto delivery system 200 and when delivery system 200 is detached and removed, proximal sheath 202A is removed with delivery system 200.

In an illustrative embodiment, gastric spacer filler device 19 is at least partially covered by two sheaths: proximal sheath 202A and distal sheath 202B. Distal sheath 202B at least partially covers distal space filler 91B until distal space filler 91B is inflated, which causes distal sheath 202B to be rolled onto itself, either toward distal end of gastric space filler device 19 or toward center of gastric space filler device 19. Similarly, proximal sheath 202A at least partially covers proximal space filler 91A until proximal space filler 91A is inflated, which causes proximal sheath 202A to be rolled onto itself, either toward proximal end of gastric space filler device 19 or toward the center of gastric space filler device 19.

In an illustrative embodiment, gastric space filler device 19 is at least partially covered by a single sheath: central sheath 202C. Central sheath 202C at least partially covers each of proximal space filler 91A and distal space filler 91B. As distal space filler 91B is inflated, central sheath 202C is rolled onto itself from proximal end of gastric space filler device 19 toward center of gastric space filler device 19 until central sheath 202C no longer covers distal space filler 91B. As proximal space filler 91A is inflated, central sheath 202C is rolled onto itself from proximal end of gastric space filler device 19 toward center of gastric space filler device 19 until central sheath 202C no longer covers proximal space filler 91A. Alternatively, as proximal space filler 91A is inflated, central sheath 202C may be rolled from center of gastric space filler device 19 toward proximal end of gastric space filler device 19.

While the apparatus and method have been described in terms of what are presently considered to be the most practical embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method of delivering a gastric space filler device, the method comprising:
attaching a delivery system to a gastric space filler device by releasably coupling a docking clip of the delivery system to a docking notch at a proximal end of an infusing member of the gastric space filler device;
delivering a guidewire through an esophagus to a stomach;
after the delivery system is attached to the gastric space filler, guiding the gastric space filler device and the delivery system together over the guidewire to the stomach;
inflating a space filler of the gastric space filler device with a fluid provided from the delivery system through an infusing lumen in the infusing member of the gastric space filler device;
detaching the delivery system from the gastric space filler device by removing the docking clip from the docking notch; and
removing the delivery system from the stomach without removing the gastric space filler device from the stomach.

2. The method of claim 1 wherein the delivery system is attached to the gastric space filler device before the gastric space filler device and the delivery system are guided along the path defined by the guidewire.

3. The method of claim 1 wherein attaching the delivery system to the gastric space filler device further comprises inserting a barb of the delivery system into a gate at the proximal end of the infusing member of the gastric space filler device.

4. The method of claim 3 wherein attaching the delivery system to the gastric space filler device comprises attaching the delivery system such that the barb provides fluid communication between a delivery lumen of the delivery system and the infusing lumen of the gastric space filler device when the barb is inserted into the gate.

5. The method of claim 3 wherein detaching the delivery system from the gastric space filler device further comprises removing the barb from the proximal end of the infusing member after at least partially inflating the space filler.

6. The method of claim 5 wherein removing the barb from the proximal end of the infusing member causes the gate to close.

7. The method of claim 1 wherein the infusing member of the gastric space filler device comprises a filler guide wire channel and the delivery system comprises a delivery guide wire channel, and wherein the method further comprises threading the guidewire through at least one of the filler guide wire channel and the delivery guide wire channel before guiding the gastric space filler device and the delivery system along the path defined by the guidewire.

8. The method of claim 7 wherein the filler guide wire channel extends from a proximal end of the infusing member to a distal end of the infusing member.

9. The method of claim 1, further comprising at least partially covering the gastric space filler device with a sheath before guiding the gastric space filler device along the guidewire.

10. The method of claim 1 wherein the infusing member extends completely through the space filler and includes a guidewire channel separate from the infusing lumen, and wherein the guidewire channel extends completely through the infusing member and is configured to receive the guidewire.

11. A gastric space filler system, comprising:
a gastric space filler device comprising
a flexible, elongate infusing member having a proximal end, a distal end, a filler guide wire channel extending completely through the infusing member from the proximal end to the distal end, and an infusing lumen separate from the filler guide wire channel;
a plurality of inflatable gastric space fillers secured to the infusing member, wherein the infusing member extends completely through the gastric space fillers; and
a docking notch at the proximal end of the infusing member; and
a delivery system having a docking clip configured to be attached over the docking notch to releasably attach the delivery system to the gastric space filler device, wherein the delivery system includes a delivery guide wire channel in communication with the filler guide wire channel and a fluid delivery lumen in communication with the infusing lumen when the delivery system is attached to the gastric space filler device.

12. The gastric space filler system of claim 11 wherein:

the plurality of inflatable gastric space fillers comprise a proximal inflatable space filler and a distal inflatable space filler;

the infusing lumen of the gastric space filler device comprises a proximal lumen in fluid communication with the proximal inflatable gastric space filler and a distal lumen in fluid communication with the distal inflatable gastric space filler; and the delivery system further comprises
- a proximal barb configured to be inserted into the proximal lumen of the infusing member and provide fluid communication between the delivery system and the proximal inflatable space filler; and
- a distal barb configured to be inserted into the distal lumen of the infusing member and provide fluid communication between the delivery system and the distal inflatable space filler.

13. The gastric space filler system of claim 12 wherein the proximal inflatable space filler and the proximal infusing lumen are not in fluid communication with the distal inflatable space filler and the distal infusing lumen.

14. The gastric space filler system of claim 11, further comprising a guidewire threaded through the filler guide wire channel and the delivery guide wire channel.

15. The gastric space filler system of claim 11 wherein at least one of the gastric space fillers has an outer diameter of at least about 40 mm when inflated with a fluid.

16. The gastric space filler system of claim 11 wherein the gastric space fillers are configured to at least partially fill a portion of a stomach of a human patient to create a feeling of satiety.

* * * * *